United States Patent
Yoshida et al.

(10) Patent No.: US 8,884,250 B2
(45) Date of Patent: Nov. 11, 2014

(54) BIOFUEL DEGRADATION SENSOR BASED ON FLUORESCENCE MEASUREMENTS

(75) Inventors: Shuntaro Yoshida, Kariya (JP); Noriyasu Amano, Gamagori (JP); Kazuhiro Wakao, Susono (JP); Mie Sasai, Susono (JP); Keiichiro Aoki, Shizuoka-ken (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 13/639,173

(22) PCT Filed: Apr. 20, 2011

(86) PCT No.: PCT/IB2011/001096
§ 371 (c)(1),
(2), (4) Date: Oct. 3, 2012

(87) PCT Pub. No.: WO2011/132079
PCT Pub. Date: Oct. 27, 2011

(65) Prior Publication Data
US 2013/0068965 A1   Mar. 21, 2013

(30) Foreign Application Priority Data
Apr. 23, 2010   (JP) .................. 2010-099799

(51) Int. Cl.
*F21V 9/16* (2006.01)
*G01N 21/00* (2006.01)
*G01N 21/64* (2006.01)
*G01N 33/28* (2006.01)

(52) U.S. Cl.
CPC ............ *G01N 21/64* (2013.01); *G01N 33/2876* (2013.01); *G01N 33/2852* (2013.01); *G01N 33/287* (2013.01); *G01N 33/2829* (2013.01); *G01N 21/643* (2013.01)
USPC .................. 250/458.1; 422/82.05; 422/82.06; 422/82.07; 422/82.08; 422/82.09

(58) Field of Classification Search
CPC .................. G01N 33/287; G01N 33/2888
USPC .................. 250/458.1; 422/82.05–82.09
See application file for complete search history.

(56) References Cited

U.S. PATENT DOCUMENTS 5,407,638 A * 4/1995 Wang .................. 422/82.09
5,843,783 A   12/1998 Rutledge et al.
(Continued)

FOREIGN PATENT DOCUMENTS

JP   08-128916 A   5/1996
JP   11-511843 A   10/1999
(Continued)

OTHER PUBLICATIONS

"Analyzing Biodiesel: Standards and Other Methods", JOACS, vol. 83, No. 10 (2006), p. 823-833 to Knothe.*

(Continued)

*Primary Examiner* — David Porta
*Assistant Examiner* — Kenneth J Malkowski
(74) *Attorney, Agent, or Firm* — Sughrue Mion, PLLC

(57) ABSTRACT

A sensor that detects a fuel property of a mixed fuel of a biofuel and a hydrocarbon fuel includes: a light emitting device that emits light with a wavelength of 250 nm to 400 nm onto the mixed fuel; and a light receiving device that receives light emitted by the mixed fuel under the effect of light from the light emitting device and generates an output corresponding to the received light. When the fuel property is determined, in a case where the mixed fuel is irradiated by light with a predetermined wavelength generated due to voltage application to the light emitting device, the light emitted by the mixed fuel is detected by the light receiving device. The fuel property of the mixed fuel is detected according to the detected light.

5 Claims, 8 Drawing Sheets

(56) References Cited

U.S. PATENT DOCUMENTS

| | | | |
|---|---|---|---|
| 6,784,988 B2 * | 8/2004 | Vijayakumar et al. | 356/244 |
| 2004/0012777 A1 | 1/2004 | Vijayakumar et al. | |
| 2007/0237679 A1 * | 10/2007 | Hegazi | 422/82.08 |
| 2009/0317299 A1 | 12/2009 | Rebinsky et al. | |

FOREIGN PATENT DOCUMENTS

| | | |
|---|---|---|
| JP | 2002-168789 A | 6/2002 |
| JP | 2005-043132 A | 2/2005 |
| JP | 2008-286531 A | 11/2008 |
| JP | 2009-281733 A | 12/2009 |
| JP | 2009-293437 A | 12/2009 |
| WO | 2006/101653 A2 | 9/2006 |
| WO | 2009/040635 A1 | 4/2009 |

OTHER PUBLICATIONS

Aliske et al.: "Measurement of biodiesel concentration in a diesel oil mixture", Fuel, IPC Science and Technology Press, Guildford, GB, vol. 86, No. 10-11, Apr. 17, 2007, pp. 1461-1464, XP022032430, ISSN: 0016-2361, DOI: 10.1016/J.Fuel.2006.11.008.

International Search Report and Written Opinion for corresponding International Patent Application No. PCT/182011/001096 mailed Aug. 25, 2011.

Japanese Office Action for corresponding JP Patent Application No. 2010-099799 issued on Dec. 8, 2011.

V. Kampars et al., "Fluorescence Spectroscopy Investigation of Degradation of Rapeseed Oil Methyl Esters", Scientific Proceedings of Riga Technical University, Material Science and Applied Chemistry, 2005, 10: 59-64.

* cited by examiner

BIOFUEL DEGRADATION SENSOR BASED ON FLUORESCENCE MEASUREMENTS

BACKGROUND OF THE INVENTION

1. Field of the Invention

The invention relates to a fuel property sensor and a fuel property detection device. More specifically, the invention relates to a fuel property sensor and a fuel property detection device advantageously suitable that detects a state of a mixed fuel of a biofuel and a hydrocarbon fuel.

2. Description of Related Art

In recent years, following the increased usage of biofuels, internal combustion engines for vehicles that can use not only a biofuel but also a mixed fuel obtained by mixing a biofuel and a hydrocarbon fuel have been researched and developed. However, the state of biofuels deteriorates rather easily with time. Therefore, it is desirable that the deterioration state of biofuels be detected when the biofuel is used.

For example, Japanese Patent Application Publication No. 2009-293437 (JP-A-2009-293437) discloses a method for determining the deterioration of a biofuel. More specifically, with the method disclosed in JP-A-2009-293437, a thermometer and a kinematic viscometer are disposed in an intake pipe of an internal combustion engine and the temperature and kinematic viscosity of the biofuel are measured. According to the description of JP-A-2009-293437, the kinematic viscosity of biofuel changes according to the deterioration state thereof, and therefore by using this principle it is possible to determine the deterioration of fuel on the basis of temperature and kinematic viscosity.

The continuous use of deteriorated fuel in an internal combustion engine using a biofuel or a mixed fuel of a biofuel and a hydrocarbon fuel as an engine fuel can result, for example, in deterioration of fuel injection valves and accumulation of deposits. Therefore, it is desirable that the fuel deterioration state be detected. However, when the deterioration of fuel is determined on the basis of kinematic viscosity of the fuel, as in the technique described in JP-A-2009-293437, a kinematic viscometer and a thermometer have to be provided only for determining fuel deterioration. As a result, the cost of fuel deterioration determination is increased.

SUMMARY OF THE INVENTION

The invention provides a fuel property sensor and a fuel property detection device that can detect a fuel property, while inhibiting the increase in the number of additional components.

The first aspect of the invention relates to sensor that detects a fuel property of a mixed fuel of a biofuel and a hydrocarbon fuel. The sensor is provided with a light emitting device disposed so as to emit light with a wavelength of 250 nm to 400 nm onto the mixed fuel; and a light receiving device that receives light emitted by the mixed fuel and generates an output corresponding to the received light.

The sensor having such light emitting device and light receiving device can detect the fuel property of the mixed fuel.

The sensor may further include: a detection unit that causes the mixed fuel to flow; and a pair of optical guiding devices disposed to face each other, with the detection unit being interposed therebetween. The light emitting device may be disposed to be in contact with a first surface of one of the pair of optical guiding devices, and to emit light onto the detection unit via the one of the pair of optical guiding devices, the first surface being on an opposite to a second surface of the one of the pair of optical guiding devices, and the second surface being exposed to the detection unit. The light receiving device may be disposed in contact with a first surface of the other one of the pair of optical guiding devices, and at a position in which light from the mixed fuel is received via the other one of the pair of optical guiding devices, the first surface being on an opposite to a second surface of the other one of the pair of optical guiding devices, and the second surface being exposed to the detection unit.

The sensor may further include; a detection unit that causes the mixed fuel to flow; and an optical guiding device disposed so that part thereof is exposed to the detection unit. The light emitting device and the light receiving device may be both disposed on a first surface of the optical guiding device, the first surface being on an opposite side to a second surface of the optical guiding device, and the second surface being exposed to the detection unit. The light emitting device may be disposed at a position of emitting light onto the detection unit via the optical guiding device; and the light receiving device may be disposed at a position of receiving light from the mixed fuel via the optical guiding device.

The emitted and received light can be reliably guided by the optical guiding device. Therefore, such a configuration makes it possible to detect the fuel property with better accuracy.

The light emitting device may include a light emitting diode (LED).

The light receiving device may include a photodiode (PD).

When a LED is used as the light emitting device or a PD is used as a light receiving device, the fuel property sensor can be reduced in size.

The second aspect of the invention relates to a fuel property detection device that detects a fuel property of a mixed fuel of a biofuel and a hydrocarbon fuel. The detection device includes a light emitting device that emits light with, a wavelength of 250 nm to 400 nm onto the mixed fuel when a voltage is applied; a voltage application device that applies the predetermined voltage to the light emitting device; a light receiving device that receives light emitted by the mixed fuel under the effect of light from the light emitting unit and generates an output corresponding to the received light; and a detection device that detects a fuel property of the mixed fuel according to the output of the light receiving device.

By using the fuel property detection device that detects light from the mixed fuel in the above-described manner it is possible to detect reliably a hydrocarbon concentration or a fuel property such as a deterioration state of the mixed fuel in use of a simpler device.

The detection device may detect a deterioration state of the mixed fuel according to the output of the light receiving device.

Thus, a deterioration state of the mixed fuel can be detected according to the output of the light receiving device. As a result, the deterioration of fuel injection valves or accumulation of deposits caused by continuous use of the deteriorated mixed fuel can be prevented.

The detection device may detect a concentration of the hydrocarbon fuel in the mixed fuel according to the output of the light receiving device.

The biofuel may include oleic acid methyl ester or linoleic acid methyl ester.

The biofuel may be a biofuel using as a starting material at least one oil from among rapeseed oil, soybean oil, palm oil, coconut oil, corn oil, and olive oil.

The hydrocarbon may be light oil.

The detection device may further include a detection unit that causes the mixed fuel to flow, and a pair of optical guiding devices disposed to face each other, with the detection unit being interposed therebetween. The light emitting device may be disposed to be in contact with a first surface of one of the pair of optical guiding devices, and to emit light onto the detection unit via the one of the pair of optical guiding devices, the first surface being on an opposite to a second surface of the one of the pair of optical guiding devices, and the second surface being exposed to the detection unit. The light receiving device may be disposed in contact with a first surface of the other one of the pair of optical guiding devices, and at a position in which light from the mixed fuel is received via the other one of the pair of optical guiding devices, the first surface being on an opposite to a second surface of the other one of the pair of optical guiding devices, and the second surface being exposed to the detection unit.

The detection device may further include a detection unit that causes the mixed fuel to flow, and an optical guiding device disposed so that part thereof is exposed to the detection unit. The light emitting device and the light receiving device may be both disposed on a first surface of the optical guiding device, the first surface being on an opposite side to a second surface of the optical guiding device, and the second surface being exposed to the detection unit. The light emitting device may be disposed at a position of emitting light onto the detection unit via the optical guiding device; and the light receiving device may be disposed at a position of receiving light from the mixed fuel via the optical guiding device.

Thus, the emitted and received light can be reliably guided by the optical guiding device. Therefore, such a configuration makes it possible to detect the fuel property with better accuracy.

The light emitting device may include a LED.

The light receiving device may include a PD.

A LED is used as the light emitting device, or a PD is used as the light receiving device. As a result, the size of the fuel property sensor can be reduced.

In accordance with the invention, the light emitting device emits light with a wavelength of 250 nm to 400 nm onto the mixed fuel, the light receiving device receives the light emitted by the mixed fuel, and the output corresponding to the received light can be outputted. In this case, the intensity of light emitted by the mixed fuel upon receiving the irradiation light changes according to the concentration of hydrocarbons in the mixed fuel or the oxidation state of the biofuel.

BRIEF DESCRIPTION OF THE DRAWINGS

The foregoing and further objects, features and advantages of the invention will become apparent from the following description of exemplary embodiment with reference to the accompanying drawings, wherein like numerals are used to represent like elements and wherein.

DETAILED DESCRIPTION OF EMBODIMENTS

Figure 1:
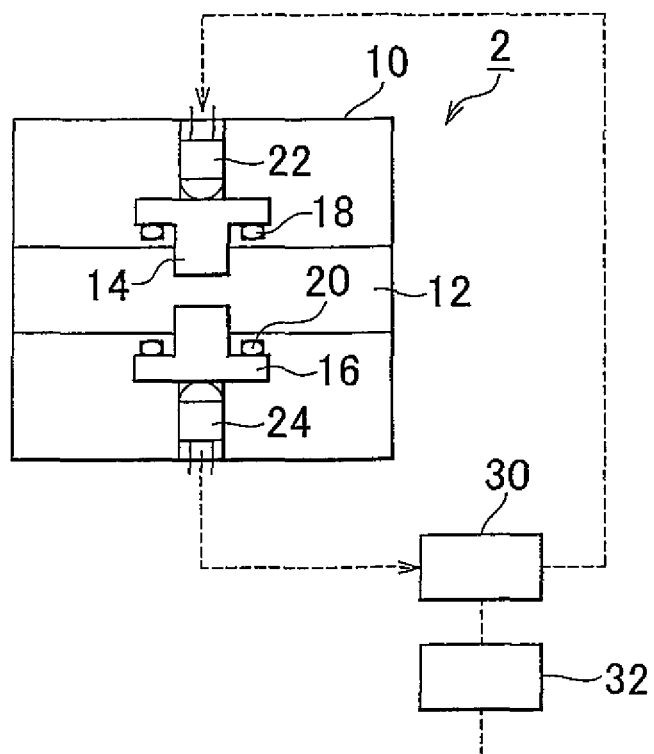
FIG. 1 is a schematic diagram illustrating the configuration of the fuel property detection device according to Embodiment 1 of the invention.

In the figures, identical or corresponding components are denoted by identical reference numerals and explanation thereof is simplified or omitted.

Embodiment 1

FIG. 1 is a schematic diagram serving to illustrate the configuration of the fuel property detection device according to Embodiment 1 of the invention. The fuel property detection device shown in FIG. 1 detects a fuel; state of a mixed fuel of biofuel and hydrocarbon fuel. In Embodiment 1, the detection of fuel property is explained with respect to a mixed fuel using Rapeseed Methyl Ester (RME) as biofuel and light oil as hydrocarbon fuel.

The fuel property detection device shown in FIG. 1 has a sensor unit 2. The sensor unit 2 has a case 10, and a detection unit 12 is formed inside the case 10. A plurality of holes (not shown in the figure) are formed in the case 10. The sensor unit 2 is disposed so that at least part thereof is exposed in a passage where the mixed fuel, which is the object of fuel property detection, flows, such as an intake pipe or an exhaust pipe of the internal combustion engine. As a result, the mixed fuel flows into the detection unit 12 via the holes formed in the case 10.

A pair of optical guiding paths (optical guiding devices) 14, 16 are disposed opposite each other so that the detection unit 12 is interposed therebetween. The optical guiding paths 14, 16 are mounted so that one surface of each optical guiding path is exposed to the detection unit 12. The optical guiding paths 14, 16 are tightly closed by respective sealing members 18, 20. As a result, the sensor unit 2 is configured such that the mixed fuel cannot leak to portions outside the detection unit 12.

A LED 22 is disposed in contact with the surface of one optical guiding path 14 on the side opposite that exposed to the detection unit 12. A PD 24 is disposed in contact with the surface of the other optical guiding path 16 on the side opposite that exposed to the detection unit 12.

An optical element drive device 30 (voltage application device) is connected to the LED 22 and the PD 24. The optical element drive device 30 applies a predetermined voltage to the LED 22 and detects a voltage from the PD 24. A signal processing device 32 (detection device) is also connected to the optical element drive device 30.

Where the predetermined voltage is applied to the LED 22 by the optical element drive device 30 in the above-described fuel property detection device, the LED 22 emits light of a predetermined wavelength. The emitted light falls via the optical guiding path 14 on the mixed fuel located in the detection unit 12. The light is then received together with the fluorescence emitted by the mixed fuel by the PD 24 via the optical guiding path 16. A voltage corresponding to the received light intensity is generated between the terminals of the PD 24, and the voltage of this PD 24 is detected by the optical element drive device 30 as the output of the PD 24. The signal processing device 32 has a function of inputting a voltage value detected by the optical element drive device 30 and detecting the fuel property in response to the inputted voltage. The principle of fuel property detection will be explained below.

FIGS. 2 to 5 serve to explain light waveforms obtained when the below-described samples 1 to 4 are irradiated with light of a plurality of wavelengths. The samples 1 to 4 that are detection objects in FIGS. 2 to 5 are as follows.

Sample 1 (FIG. 2): a mixed fuel obtained by mixing 30% RME; in this mixed fuel, the oxidation has not advanced to a total acid number of 0.06.

Sample 2 (FIG. 3): light oil.

Sample 3 (FIG. 4): RME.

Figure 2:
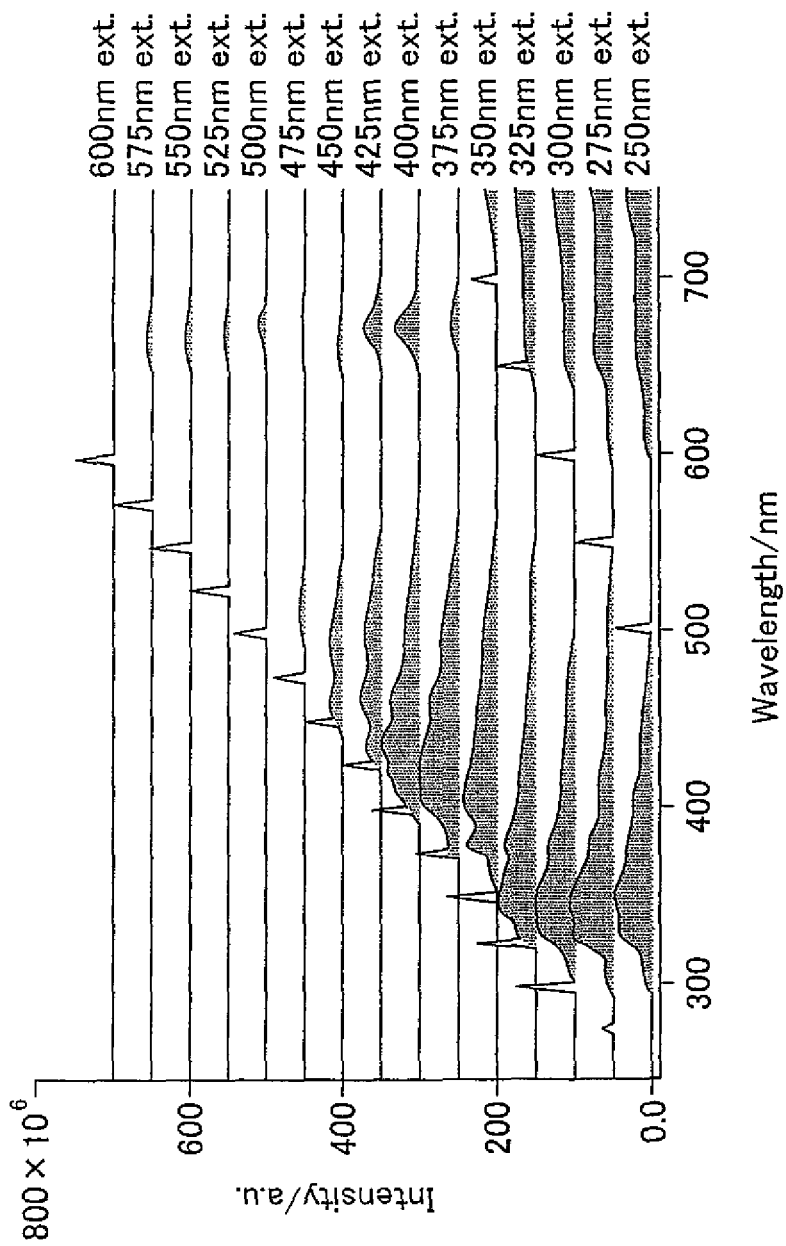
FIG. 2 illustrates the wavelengths of each obtained light when a sample 1 is irradiated with light of a plurality of wavelengths in Embodiment 1 of the invention.
Figure 3:
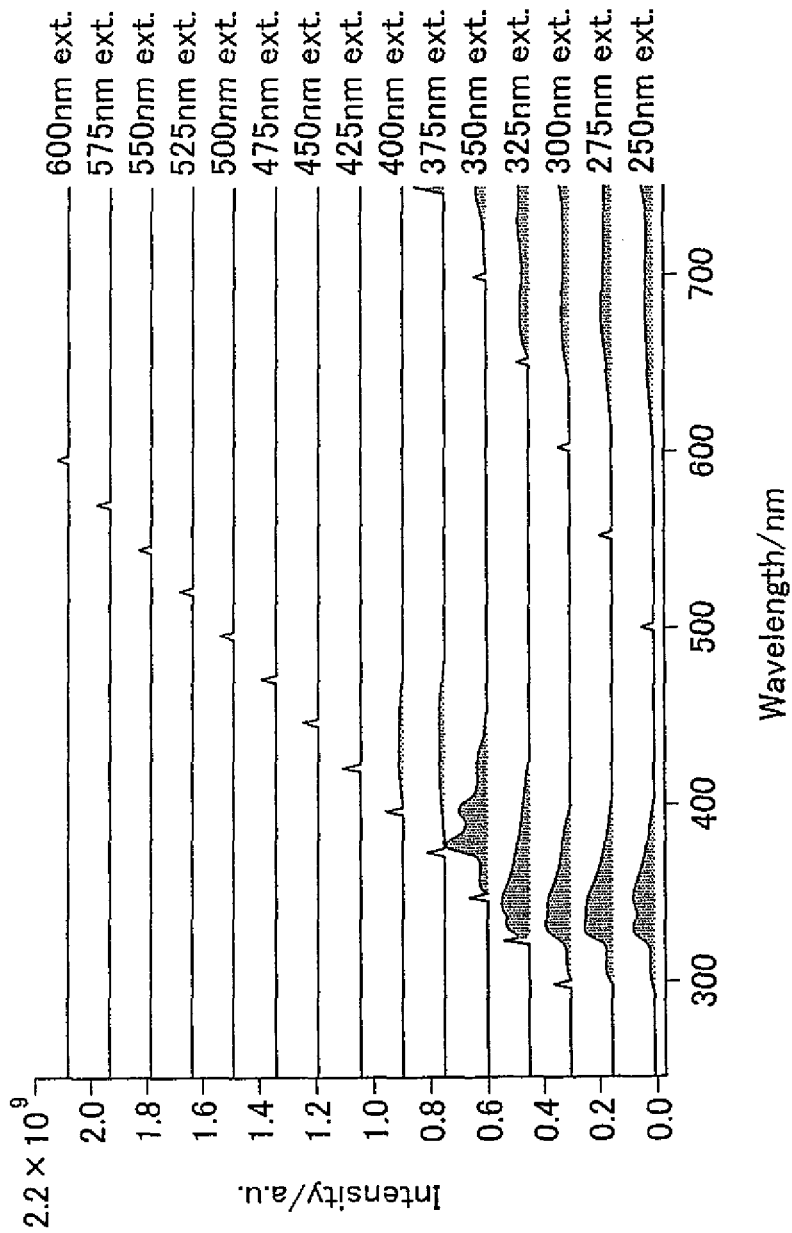
FIG. 3 illustrates the wavelengths of each obtained light when a sample 2 is irradiated with light of a plurality of wavelengths in Embodiment 1 of the invention.

Sample 4 (FIG. 5): a mixed fuel with a RME content of 30% that is identical to the mixed fuel illustrated by FIG. 2, except that the oxidation has advance to a total acid number of 6.2.

In FIGS. 2 to 5, the wavelength (nm) of light detected by the PD is plotted against the abscissa; the intensity (Intensity/a.u.) of the detected light is plotted against the left ordinate, and the wavelength (nmext.) of light emitted correspondingly to each waveform line is plotted on the right ordinate.

FIG. 2 demonstrates that when the mixed fuel of sample 1 in which the oxidation has not advanced is irradiated with light with a wavelength of 250 nm to 400 nm, fluorescence with a wavelength within a range of 300 nm to 500 nm is emitted. Further, FIG. 3 demonstrates that the light oil of sample 2 also emits fluorescence with a wavelength within a range of 300 nm to 500 nm when irradiated with light with a wavelength of 250 nm to 400 nm.

Figure 4:
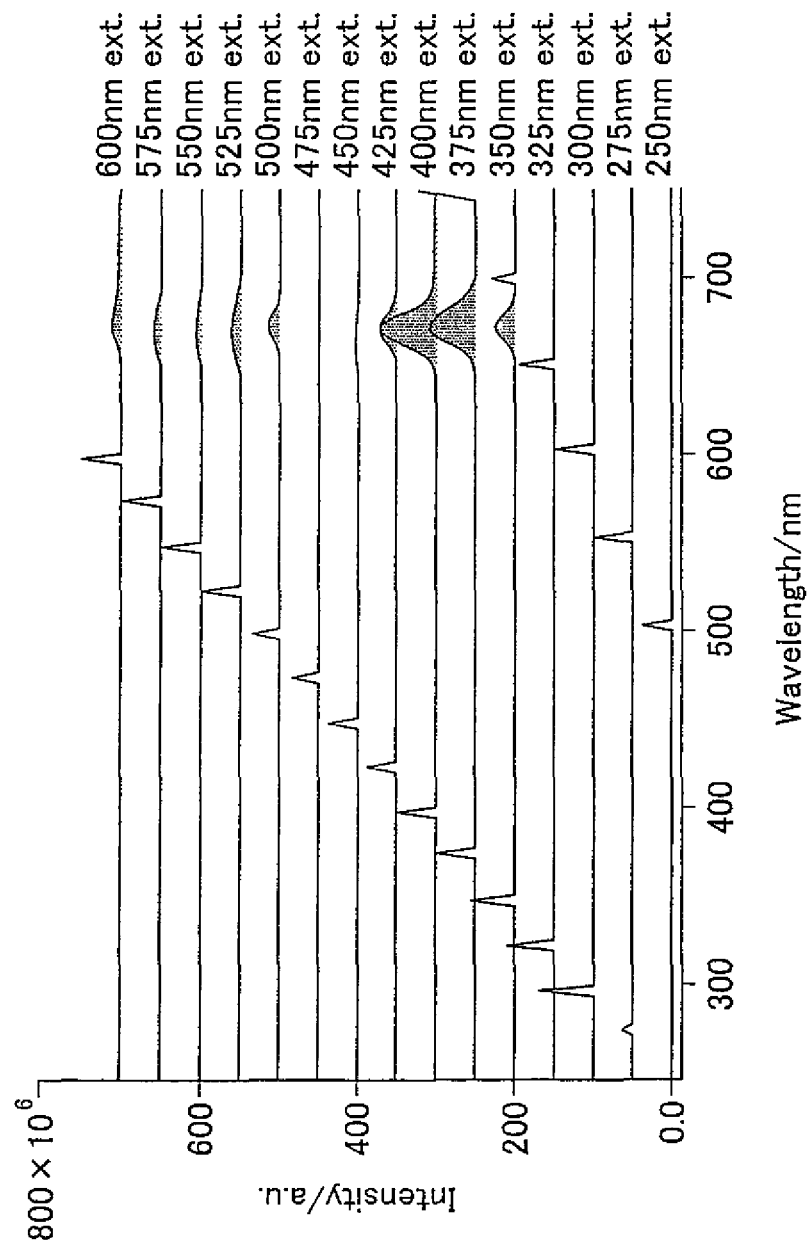
FIG. 4 illustrates the wavelengths of each obtained light when a sample 3 is irradiated with light of a plurality of wavelengths in Embodiment 1 of the invention.

FIG. 4 demonstrates that the RME of sample 3 emits no fluorescence with a wavelength within a range of wavelength equal to or less than 650 nm in response to irradiation with light with a wavelength of 250 nm to 600 nm. Thus, it can be assumed that only the light oil contained in the mixed fuel emits fluorescence in response to irradiation of the mixed fuel with light with a wavelength of 250 nm to 400 nm.

Figure 5:
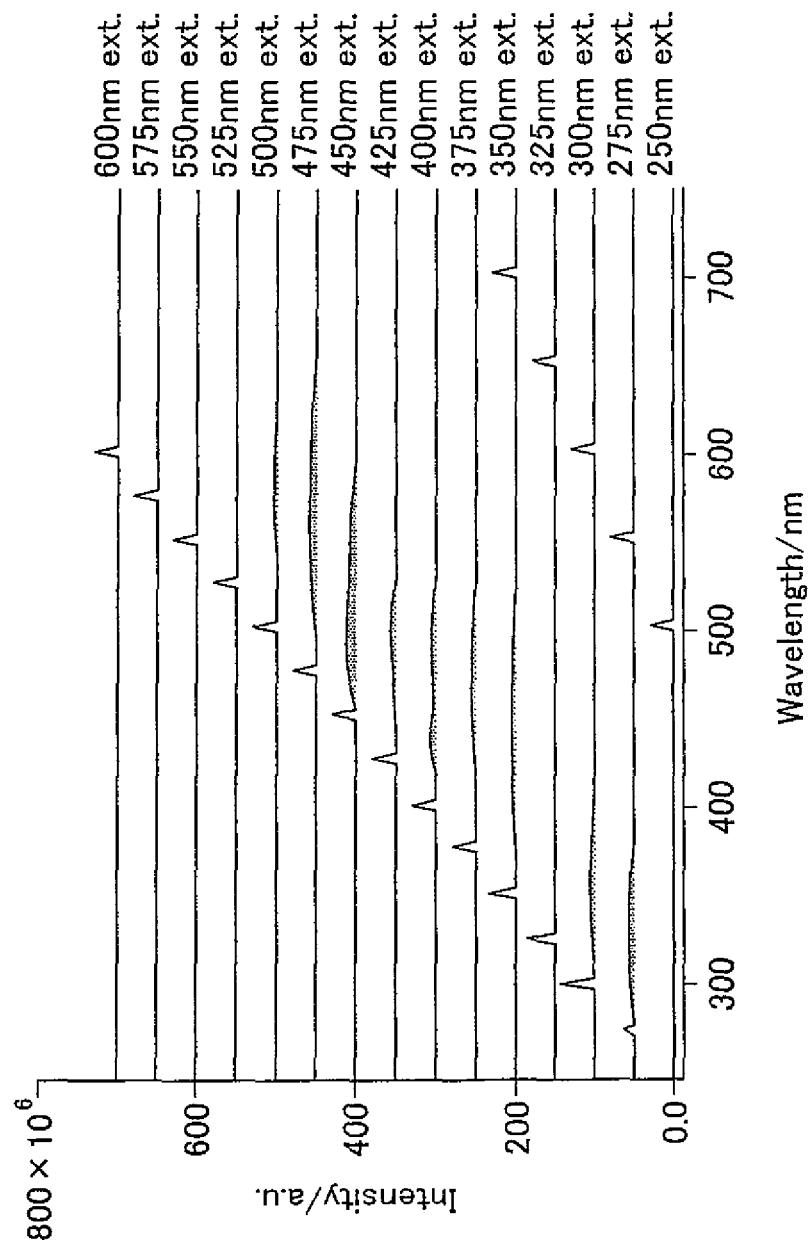
FIG. 5 illustrates the wavelengths of each obtained light when a sample 4 is irradiated with light of a plurality of wavelengths in Embodiment 1 of the invention.

Further, FIG. 5 indicates that in the case of a mixed fuel with advanced oxidation (sample 4), extremely small emission is observed even under irradiation with light with a wavelength of 250 nm to 400 nm. Thus, in the mixed fuels (sample 1, sample 4) with the same mixing ratio, fluorescence is emitted when the oxidation has not advanced (FIG. 2), but when the oxidation-induced deterioration has advanced, the intensity of emitted fluorescence apparently decreases (FIG. 5). This is apparently because the fluorescence emitted by the light oil contained in the mixed fuel is absorbed by the oxidized biofuel.

It follows from above that the fluorescence emitted by the mixed fuel changes correspondingly to the amount (ratio) of the hydrocarbon fuel, and the absorption amount of the emitted fluorescence apparently changes according to the degree of biofuel oxidation.

Figure 6:
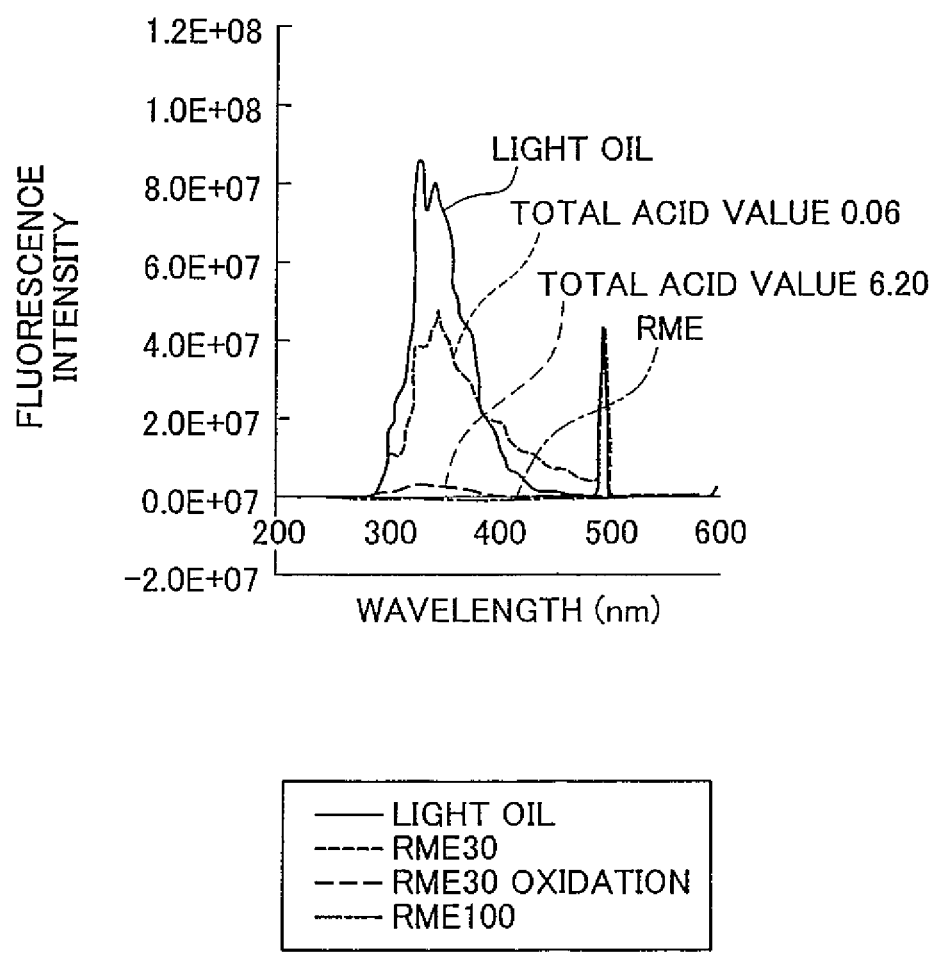
FIG. 6 provides comparative explanation of spectra of received light in the case in. which sample 1 to sample 4 are irradiated with light with a wavelength of 250 nm in Embodiment 1 of the invention.
Figure 7:
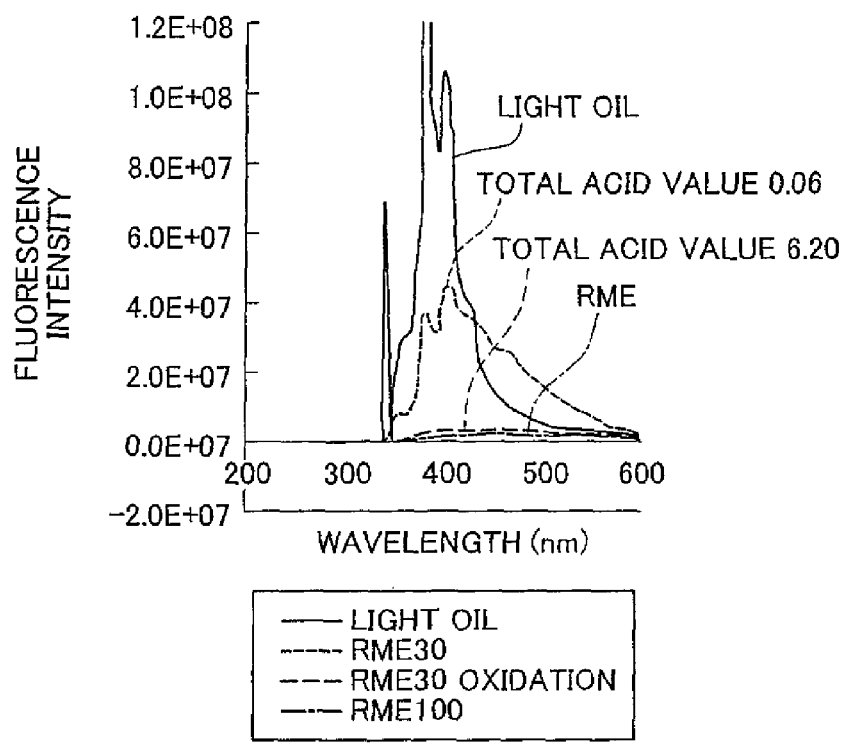
FIG. 7 provides comparative explanation of spectra of received light in the case in which sample 1 to sample 4 are irradiated with light with a wavelength of 350 nm in Embodiment 1 of the invention.

Spectra of light detected when the aforementioned sample 1 to sample 4 are irradiated with light of two different wavelengths will be discussed below by way of example. FIG. 6 shows spectra of light obtained under irradiation of samples 1 to 4 with light with a wavelength of 250 nm. Likewise, FIG. 7 shows spectra of light obtained under irradiation with light with a wavelength of 350 nm. In FIGS. 6 and 7 the wavelength (nm) of detected light is plotted against the abscissa, and the intensity (a.u.) of detected light is plotted against the ordinate.

As shown in FIGS. 6 and 7, with either wavelength, the intensity of emitted fluorescence in case of 100% light oil (sample 2) is higher than that in the case of the fuel in a mixture with 30% RME (sample 1), and practically no fluorescence is emitted in the case with RME 100%. A comparatively strong fluorescence is detected at a wavelength of 300 nm to 500 nm in the unoxidized mixed fuel of sample 1, but when the oxidation of mixed fuel has advanced (sample 4), the intensity of detected light decreases significantly with respect to that of the unoxidized fuel (sample 1).

Thus, the intensity of fluorescence emitted by the mixed fuel changes according to the concentration of light oil in the mixed fuel, and the adsorption amount of the fluorescence changes according to the oxidation degree of the biofuel. In other words, the intensity of light detected by the PD 24 from the mixed fuel is correlated with the fuel concentration of the mixed fuel and the oxidation state of the biofuel.

Figure 8:
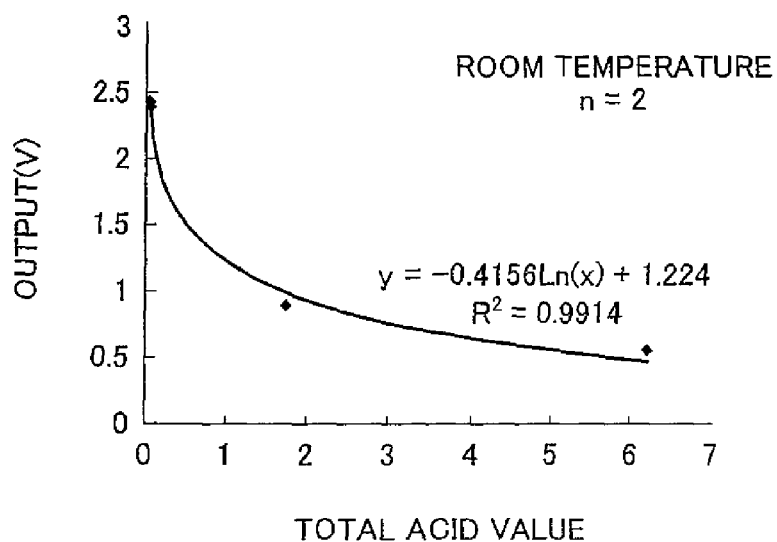
FIG. 8 illustrates the relationship between a total acid value of the biofuel and the output produced by PD in Embodiment 1 of the invention.

FIG. 8 illustrates the light intensity detected in the case in which mixed fuels of the same concentration but different total acid value are irradiated with light of a predetermined wavelength. In FIG. 8, the total acid value is plotted against the abscissa, and the output value (v) of PA corresponding to the light intensity is plotted against the ordinate. More specifically, in the example shown in FIG. 8, a configuration is used in which a LED emitting ultraviolet radiation with a central wavelength of 365 nm and an irradiation wavelength of 350 nm to 400 nm and a PD having sensitivity at a wavelength of 300 nm to 1000 nm are disposed in a cell with an optical path length of 1 mm and the output of PD is detected when the mixed fuel is irradiated with light of the LED. FIG. 8 demonstrates that the output of PD decreases with the increase in the total acid value of the mixed fuel. Thus, FIG. 8 confirms the correlation between the total acid value (deterioration state) of the mixed fuel and the light intensity.

Therefore, for example, where the concentration of light oil in the mixed fuel at the initial stage is identified, it is possible to detect the present deterioration state caused by oxidation of the mixed fuel by detecting with the PD 24 the intensity of fluorescence emitted by the mixed fuel. In the signal processing device 32 of Embodiment 1, the relationship between the output of the PD 24 in the case of irradiation with light of a predetermined wavelength (250 nm to 400 nm), such as shown in FIG. 8, and the total acid value of the mixed fuel is stored in advance for each fuel concentration of the mixed fuel. Therefore, by irradiating with light of the predetermined wavelength and detecting the output of PD 24, it is possible to determine the total acid value corresponding to the output of the PD 24. As a result, the deterioration state of the mixed fuel can be determined.

The correlation of the intensity of fluorescence and the concentration of light oil in the mixed fuel can be also considered. Therefore, in the state without absorption of the fluorescence emitted by the biofuel, that is, in the initial state in which the mixed fuel has not been deteriorated, it is possible to detect the concentration of light oil in the mixed fuel by detecting the intensity of fluorescence. In Embodiment 1, the relationship between the output value of the PD 24 corresponding to the predetermined wavelength and the concentration of light oil (or RME concentration) in the mixed fuel is stored in the signal processing device 32. When the mixed fuel is added, it is possible to detect the concentration of light oil in the added mixed fuel by detecting the intensity of fluorescence emitted by the admixed mixed fuel.

As described hereinabove, in Embodiment 1 of the invention, the total acid value of the mixed fuel or the concentration of light oil in the admixed mixed fuel can be determined correspondingly to the output of the PD 24. Therefore, the deterioration state of the mixed fuel can be reliably detected and adhesion of deposits and corrosion of fuel injection devices occurring due to use of fuel with advance degree of oxidation can be prevented. Further, when the mixed fuel is further added, the concentration of light oil or RME in the mixed fuel can be detected. Therefore, a mixed fuel with a concentration outside the suitable range can be prevented from being admixed. In addition, since the concentration of fuel and the deterioration state of the mixed fuel can be detected with same device, the system can be simplified.

Further, in Embodiment 1, the case is explained in which a fuel having light oil and RME mixed therein is used as the mixed fuel. However, the invention is not limited to such composition and can be applied to a mixed fuel in which other hydrocarbon fuels and biofuels are mixed. For example, a fuel including a methyl ester of oleic acid or a methyl ester of linoleic acid can be used as the biofuel. More specifically, in addition to RME, which is a methyl ester derived from rapeseed oil, methyl ester derived from soybean oil (SME), or biofuels obtained by using palm oil, coconut oil, corn oil, and olive oil as starting materials can be used as the biofuel.

Even when other biofuels or other hydrocarbon fuels are used, when the mixed fuel is irradiated with light of a predetermined wavelength, the mixed fuel emits fluorescence corresponding to the ratio of hydrocarbon fuel in the mixed fuel and absorbs the fluorescence correspondingly to the degree of oxidation of the biofuel in the same manner as the mixed fuel of light oil and RME.

Therefore, the deterioration of fuel can be determined correspondingly to the output of the PD 24 by examining experimentally in advance the relationship between the output value of the PD 24 and the total acid value in the case in which the fuel is irradiated with light of a predetermined wavelength for each concentration of the hydrocarbon fuel (or biofuel) in the mixed fuel and storing this relationship in the signal processing device 32, in the same manner as in the case explained in Embodiment 1. Further, the concentration of mixed fuel can be also detected by examining in advance the relationship between the concentration of hydrocarbon fuel in the mixed fuel at the initial stage (non-oxidized state) and the output value of the PD 24 and storing the relationship in the signal processing device 32.

Further, in Embodiment 1, the case is explained in which the LED 22 is used as the light emitting device, and the PD 24 is used as the light receiving device. However, the invention is not limited to such a configuration. Thus, other light emitting devices can be used, provided that light with a wavelength within an appropriate range can be emitted. Further, light receiving devices other than the PD 24 can be also used, provided that they can receive the emitted fluorescence and produce an output corresponding thereto.

Further, in Embodiment 1, the case is explained in which the LED 22 and the PD 24 are arranged opposite each other and have disposed therebetween the detection unit 12 having the fuel flowing therethrough. However, the invention is not limited to such a configuration.

Figure 9:
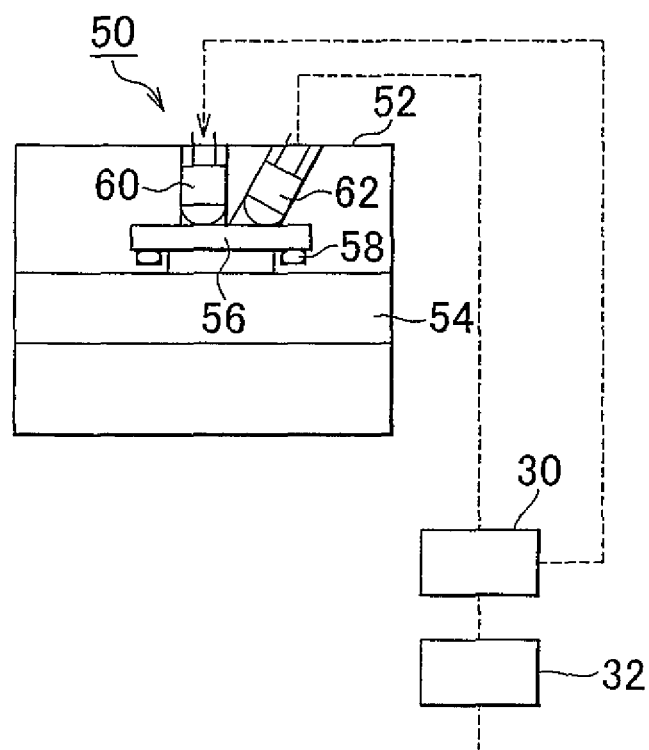
FIG. 9 is a schematic diagram for explaining another example of the fuel property detection device in Embodiment 1 of the invention.

FIG. 9 illustrates another fuel property detection device of Embodiment 1 of the invention. In the fuel property detection device shown in FIG. 9, the arrangement of the optical guiding unit and the sensor unit such as LED and PD is different from that of the sensor unit 2 shown in FIG. 1.

As shown in FIG. 9, a sensor unit 50 of this fuel property detection device has a detection unit 54 inside a case 52. An optical guiding path 56 is disposed at the detection unit 54, with a sealing member 58 being interposed therebetween. The optical guiding path 56 is disposed so that one surface thereof is exposed at the detection unit 54 side. A LED 60 and a PD 62 are disposed so as to be in contact with the surface on the side opposite that of the aforementioned one surface of the optical guiding path 56.

In the sensor unit 50, the mixed fuel located inside the detection unit 54 is irradiated with the light emitted from the LED 60 via the optical guiding path 56. The light including the fluorescence emitted by the mixed fuel is guided by the optical guiding path 56 and received by the PD 62.

In such a configuration, the light emitted by the mixed fuel can be also detected reliably, thereby making it possible to detect the concentration of each fuel component of the mixed fuel and the total acid value of the mixed fuel. Further, in the invention, the sensor is not limited to the configuration shown in FIGS. 1 and 9 and may have different configuration, provided that light can be emitted toward the mixed fuel and the emitted fluorescence can be detected.

When numbers relating to the number of elements, numerical values, quantities, ranges, etc. are mentioned in the above-described embodiment, the invention is not limited to the mentioned numbers, unless explicitly stated otherwise or when the invention is clearly specified by the numbers in principle. Further, the structure explained in the embodiment is not necessarily mandatory for attaining the object of the invention, unless explicitly stated otherwise or when the invention is clearly specified by the structure.

The invention claimed is:

1. A fuel property detection device that detects a fuel property of a mixed fuel of a biofuel and a hydrocarbon fuel, comprising:
   a light emitting device that receives a voltage application and emits light with a wavelength of 250 nm to 400 nm onto the mixed fuel;
   a voltage application device that applies a predetermined voltage to the light emitting device;
   a light receiving device that receives light emitted by the mixed fuel and generates an output corresponding to the received light; and
   a detection device that detects an oxidation state of the mixed fuel according to an intensity of light emitted by the mixed fuel.

2. The fuel property detection device according to claim 1, wherein the light emitting device includes a LED.

3. The fuel property detection device according to claim 1, wherein the light receiving device includes a PD.

4. The fuel property detection device according to claim 1, further comprising:
   a detection unit that causes the mixed fuel to flow, and
   a pair of optical guiding devices disposed to face each other, with the detection unit being interposed therebetween, wherein
   the light emitting device is disposed to be in contact with a first surface of one of the pair of optical guiding devices, and to emit light onto the detection unit via the one of the pair of optical guiding devices, the first surface being on an opposite to a second surface of the one of the pair of optical guiding devices, and the second surface being exposed to the detection unit and,
   the light receiving device is disposed in contact with a first surface of the other one of the pair of optical guiding devices, and at a position in which light from the mixed fuel is received via the other one of the pair of optical guiding devices, the first surface being on an opposite to a second surface of the other one of the pair of optical guiding devices, and the second surface being exposed to the detection unit.

5. The fuel property detection device according to claim 1, further comprising:
   a detection unit that causes the mixed fuel to flow, and
   an optical guiding device disposed so that part thereof is exposed to the detection unit, wherein
   the light emitting device and the light receiving device are both disposed on a first surface of the optical guiding device, the first surface being on an opposite side to a second surface of the optical guiding device, and the second surface being exposed to the detection unit;
   the light emitting device is disposed at a position of emitting light onto the detection unit via the optical guiding device; and
   the light receiving device is disposed at a position of receiving light from the mixed fuel via the optical guiding device.

* * * * *